United States Patent [19]

Goldman

[11] Patent Number: 5,716,330
[45] Date of Patent: Feb. 10, 1998

[54] BODY AND LIMB POSITION/MOTION DETECTOR AND POWER ASSIST APPARATUS AND METHOD

[76] Inventor: David A. Goldman, 538 Croton Heights Rd., Yorktown Heights, N.Y. 10598

[21] Appl. No.: 502,136

[22] Filed: Jul. 13, 1995

[51] Int. Cl.$^6$ ............................................. A61F 2/70
[52] U.S. Cl. .................. 601/26; 601/5; 623/24; 482/51
[58] Field of Search ............... 482/6, 7, 9, 901, 482/903, 51, 66; 601/5, 40, 23, 33–35, 26; 623/24, 30, 25, 39, 44, 57–60

[56] References Cited

U.S. PATENT DOCUMENTS

| | | |
|---|---|---|
| 3,323,518 | 6/1967 | Swanson . |
| 3,902,480 | 9/1975 | Wilson . |
| 3,940,803 | 3/1976 | Weis et al. ........................ 623/25 X |
| 4,487,199 | 12/1984 | Saringer . |
| 4,653,479 | 3/1987 | Maurer . |
| 4,872,665 | 10/1989 | Chaleire ........................... 601/35 X |
| 4,934,694 | 6/1990 | McIntosh . |
| 5,112,296 | 5/1992 | Beard et al. ..................... 482/51 X |
| 5,117,814 | 6/1992 | Luttrell et al. . |
| 5,179,939 | 1/1993 | Donovan et al. . |
| 5,254,060 | 10/1993 | Bohanan ............................ 482/60 |
| 5,255,188 | 10/1993 | Telepko . |
| 5,303,696 | 4/1994 | Boice . |
| 5,376,128 | 12/1994 | Bozeman .......................... 623/24 |

OTHER PUBLICATIONS

"Servo–Controlled Exoskeleton Measures Muscle Forces," *Control Engineering* 15 (10): 92.

Miller et al. "Weak Muscle Control of Powered Orthotic Devices" *Proceedings of the 23rd Annual Conference on Engineering in Medicine & Biology*, Washington D. C. Nov. 15–19, 1970.

*Primary Examiner*—Richard J. Apley
*Assistant Examiner*—John Mulcahy
*Attorney, Agent, or Firm*—John H. Crozier

[57] ABSTRACT

In a preferred embodiment, a power assist device for a partially or totally disabled body member, including: detection apparatus to detect position of the body member; and power assist apparatus, responsive to the detection apparatus, to provide powered assistance to move the body member in response to detection of the position of the body member and in response to the rate of change of position of the body member reaching a predetermined limit and/or in proportion to the rate of change of position of the body member.

22 Claims, 4 Drawing Sheets

BODY AND LIMB POSITION/MOTION DETECTOR AND POWER ASSIST APPARATUS AND METHOD

BACKGROUND OF THE INVENTION

1. Field of the Invention

The present invention relates to power assist for body and/or limb motion of partially or totally disabled persons generally and, more particularly, but not by way of limitation, to novel body and limb motion detector and power assist apparatus and method.

2. Background Art

A number of motorized mechanical devices have been developed for the purpose of exercising and stretching partially or totally disabled body members. Such devices are typically of a passive nature and do not assist otherwise normal movement of such body members. Most such devices are relatively complicated, are not easily portable, and consume relatively large amounts of electrical power.

Accordingly, it is a principal object of the present invention to provide power assist apparatus and method for partially or totally disabled body members.

A further object of the invention is to detect motion of a partially disabled body member and to provide power assist in response to detection of motion.

An additional object of the invention is to provide motion detection and power assist apparatus that is easily portable, lightweight, and consumes little electrical power.

Another object of the invention is to provide motion detection and power assist apparatus that is economical to construct.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a power assist device for a partially or totally disabled body member, comprising: means to detect position of said body member; and means, responsive to said means to detect, to provide powered assistance to move said body member in response to detection of said position of said body member.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which.

DETAILED DESCRIPTION OF THE PREFERRED EMBODIMENTS

Figure 1:
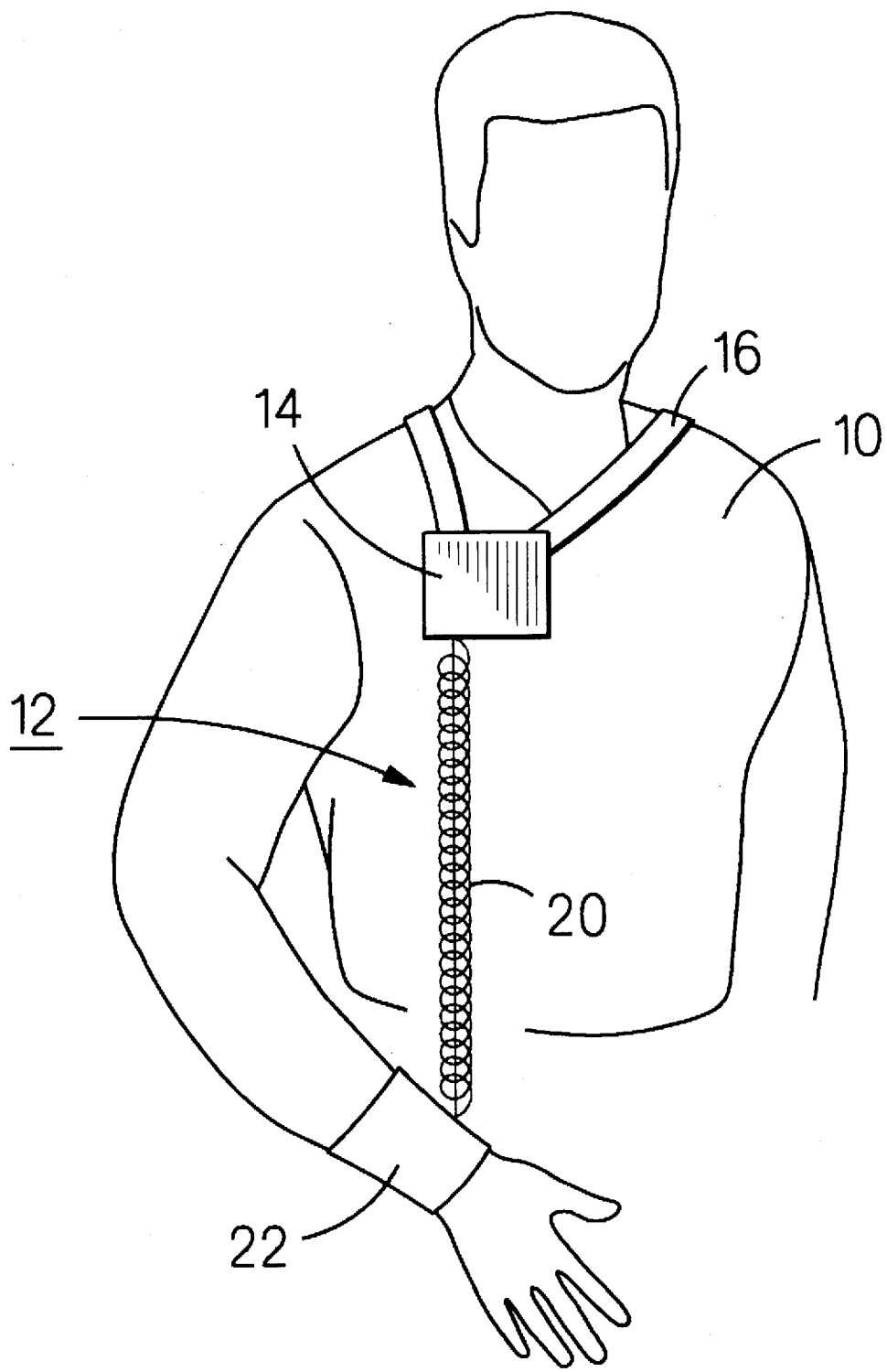
FIG. 1 is front elevational view of a person with the invention of the present invention arranged to provide power assist to the right arm of the person.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

Referring to FIG. 1, there is illustrated a person 10 with the device of the present invention, generally indicated by the reference numeral 12, arranged to provide power assist to the right arm of the person. The "arm" may include a prosthetic element (not shown). Device 12 includes a control unit 14 mounted on person 10 by means of a harness 16 encircling the neck of the person and a cable 20 extending between the control unit and a cuff 22 attached to the right wrist of the person. Power assist to the arm is provided by control unit 14 withdrawing and extending cable 20 to lift or lower the arm. While device 12 is shown as arranged to provide power assist to an arm, it will be understood that the device can be similarly arranged to provide power assist to another body member having partial or full limitation in motion, such as the neck, the back, or a leg, to utilize a variable support to achieve motion of the body member. Other means of mounting control unit 14 are also within the contemplation of the present invention. Unit 14 and cable 20 is shown as being external to clothing worn by person 10, but these elements could also be positioned under loose clothing.

As is described more fully below, there are three possible modes of operation:

The first and most significant aspect of the invention is motion sensing and power assist in which the slightest motion of the disabled body member is sensed and the rate of motion is used to control power assist movement of the body member in conformance with the user's motion. Assisted motion stops when the user restrains motion momentarily with his own controlled body member (if possible), or uses a nondisabled body member (e.g., the other arm) to restrain the controlled body member and hence stop motion. Also, motion may be initiated either by using the minute motion the user may be capable of producing, or employing a nondisabled body member to start movement (up or down). Slight reversal of motion also causes assisted motion to cease. To avoid reverse course of motion, inhibit and delay circuits are employed.

In an exercise mode, a body member can be moved continually under unit control for a period of time through a range of motion, the object being to reduce spasm and discomfort.

In a third mode, simple bi-directional control is provided by depressing switches on the unit with a non-paralyzed (or even partially restricted) hand.

Figure 2A:
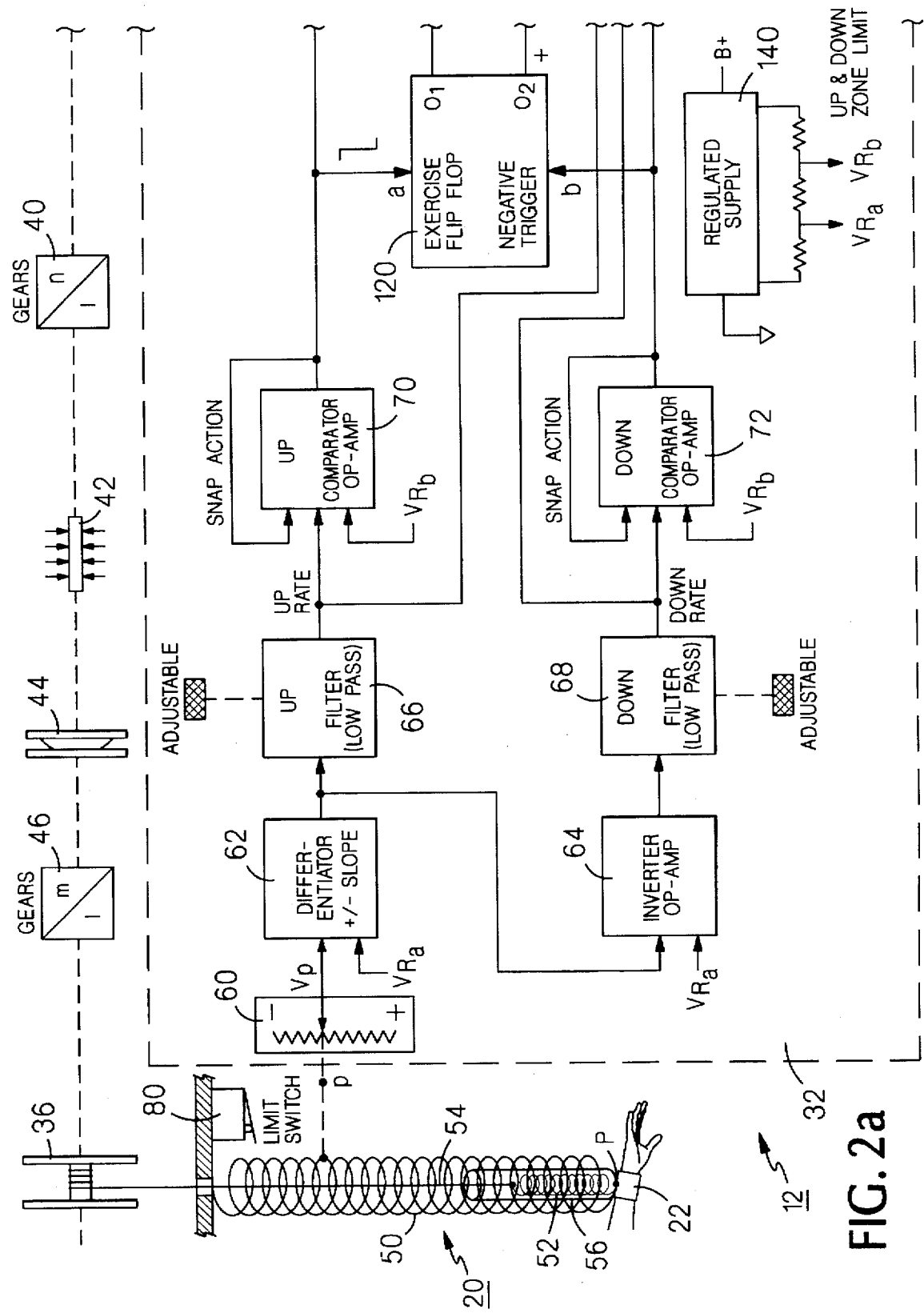
FIG. 2 is a block/schematic diagram illustrating the components and operation of a device constructed according to the invention, wherein power assist is provided in proportion to rate of motion of the arm.
Figure 2B:
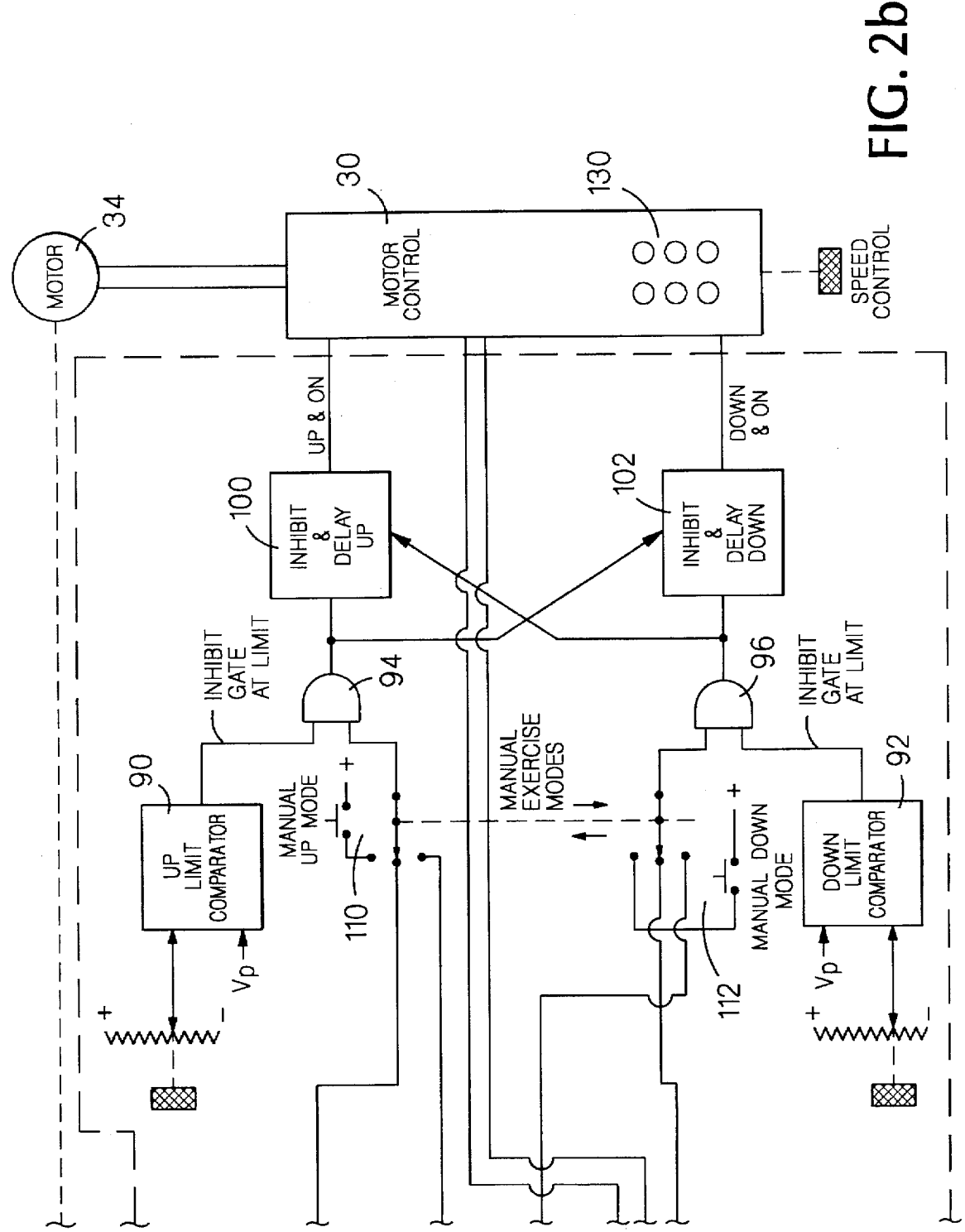

Referring now to FIG. 2, the operative elements of device 12 are illustrated and include a motor control 30 which receives "UP" and "DOWN" input signals from detection and control circuitry 32 and provides power to an electric motor 34. Motor 34 is connected to effect rotation of a pulley 36 through, in order, a first set of gears 40, a shaft friction brake 42, a slip clutch 44, and a second set of gears 46. It will be understood that the elements described so far with reference to FIG. 2 are housed in control unit 14 (FIG. 1). Control unit 14 is preferably about 1 inch deep by 3 inches high by 3 inches wide and weighs about 12–16 ounces.

Cable 20 includes a primary spring 50 connected between control unit 14 (FIG. 1) and cuff 22 and a shorter secondary spring 52 with one end also connected to the cuff and the other end connected to a thin, flexible Nylon wire 54 disposed axially internally of the the primary spring, with the proximal end of the wire attached to the distal end of the secondary spring, and with the distal end of the wire connected to pulley 36. Primary spring 50 is about 5/8 inch in diameter and, for the arrangement shown, varies in length from about 5 inches when compressed to about 16 inches when fully extended. A cylindrical tube 56 may be disposed between spring 50 and 52 to provide some frictional damping. Mechanisms other than cable 20 are also possible, such as a telescoping lead screw or a notched belt.

Unique aspects of the cable in this configuration are threefold. First, since primary spring 50 is linear, monitoring a small segment (e.g., the ½–1 inch closest to control unit 14), mirrors in miniature, p, the extreme position variation, P, of the primary spring connected to cuff 22 and, hence, wrist position. Therefore, with a sensing device such as a potentiometer 60 (or optical or magnetic sensor, etc.) connected or referenced to primary spring 50 as shown, the extreme position, P, may be inferred. In this case, the output of potentiometer 60 is roughly linear, using approximately a +/−20-degree movement, corresponding to a 5–16-inch spring extension range. Since, in a linear spring, force is proportional to displacement, per Hook's Law, a force detection sensor is also feasible.

Using the output, p, of potentiometer 60, position P may be effectively time differentiated by differentiation circuitry 62 to determine the up and down rate of motion of the wrist. The output "UP RATE" is inverted by an operational amplifier 64 to produce "DOWN RATE". Adjustable filters 66 and 68 are provided for spasticity and transient damping. Note that filter negative outputs have no effect on succeeding comparators 70 and 72.

"UP RATE" and "DOWN RATE" signals are applied, respectively, to operational amplifier comparators 70 and 72, so that when a comparator threshold is exceeded (corresponding to a persistent rate of P), one or the other comparator controls the on-off and rotational direction of motor 34 which controls, in turn, cable 20 and, hence, cuff 22 and the lower arm of the user (FIG. 1). Filters 66 and 68 may be adjusted manually for individual users. When the rate of P reduces below a second threshold (which may differ from the "on" threshold indicated on FIG. 2), due to the snap action switch of comparator 70 or 72, or the rate reduces rapidly, motor 34 is stopped, leaving the arm in the desired position. Since the motor drive is held by friction brake 42, or other means, limited only by slip clutch 44, the arm may be positioned in this manner anywhere within the range of primary spring 50. In the upward direction, motor 34 turns off when primary spring 50 cannot compress further and motion stops. A limit switch 80 may be employed in case slip clutch 44 doesn't operate properly.

In the downward direction, control 30 turns off motor 34 when the arm reaches its extreme position due to gravity or user control (since the velocity of P is zero). However, the delay in turning off (a fraction of a second) may cause cable 20 to slacken, and, therefore, subsequently require a moment to raise the arm in the upward direction. To reduce this, the signal representing position, p, from potentiometer 60 may be applied to an operational amplifier comparator 90 set to gate off the motor control circuit before the extreme lower position is reached. Another operational amplifier comparator may be used to adjust the upward stop position before the limit switch is engaged (if desired).

The second important aspect of the spring action of springs 50 and 52 is to provide an artificial tonus (the natural condition of muscle at rest) to the body member if it is paralyzed or partially unusable or flaccid.

The third advantage of the spring action is that it reduces the load on the motor drive, aiding when most required. In the extreme position of a body member (hand or foot down, for example), where the angle between the spring and the limb is smallest, the force required to raise the body member is greater and spring tension is correspondingly greater. The shorter secondary spring 52 permits the user to move the body member down at any position to produce a negative controlling rate signal if desired. Without secondary spring 52, cable 20 (unless otherwise elastic) would not permit downward motion, since pulley 36 is held by friction or other type of gearing when motor 34 is off (unless the force exceeds the setting of slip clutch 44). Although springs are described in a preferred embodiment, roughly proportional elastic material may be employed (e.g., rubber).

A major feature of device 12 is that power assist can be controlled solely by rate of motion as described above, thus not requiring individual limit settings for each user. However, not basic to the invention, individualized position limits may be set using the output, $V_p$, of potentiometer 60 with comparators 90 and 92, using the comparator outputs to gate off the motor control signals through AND gates 94 and 96, respectively, at set limits. If the user moves his body member inward from the limits, motion controlled by rate will again automatically control the arm. Inhibit and delay circuits 100 and 102 introduce a slight delay at termination of motion in the up or down directions, respectively, to prevent reverse course of motion.

Switches 110 and 112 are shown in position for the normal mode of rate operation, as described above; however, control circuitry may be provided for each in order to override the normal rate operation in either up or down direction, with detection and control circuitry 32 returning to rate mode when the manual switches are released. In a third position, switches 110 and 112 permit an exercise flip flop 120 to move the arm of person 10 (FIG. 1) continually through a selected range of motion.

A plurality of switch buttons 130 is provided on motor control 30 for "on" and "off" functions, as well as mode selection, and to provide for simple bi-directional control apart from inputs from position and control circuitry 34.

In order to provide power assist in proportion to rate of motion, the outputs of filters 66 and 68 are connected directly to motor control 30.

Batteries in motor control and power supply 30 may be in pack form and removable for recharging or replacement, or rechargeable within the unit, employing low voltage and well known charging techniques.

Device 12 preferably weighs less than a pound, and is designed such that the same unit (reversed from front to back) can be used for either arm, for example. In that case, controls for the alternate hand may be positioned on the inner side vertical surface of control unit 14 to facilitate control by the alternate hand.

A version of device 12 (or possibly even the same unit) may be used to assist in the motion of a leg limited in movement, where the limitation is possibly caused by a stroke, for example, in a manner similar to the arm assist described above. For example, a hinged knee brace type of harness can be used to mount a unit at the outside (possibly inner side) of the lower thigh with the springs connected to the back portion of a shoe. As the foot is raised slightly in walking, the unit raises the leg to a preset limit, and when released (even by ever so slight user action) returns to the ground, turning the motor off, since the rate at that point is zero (or very low). Motor speed may be manually adjusted depending on the user's gait. Special adaptive type circuits or a microprocessor may be employed to modify speed in a more sophisticated version.

Device 12 preferably operates normally for at least a day with about a 1–2 hour total motor running time using four size AA batteries, and can be readily recharged at night. A recharging connector and switch (not shown) in device 12 can permit the unit to be operated during recharge or to deactivate the circuitry during a period such as the night when the unit is not worn and the battery is being recharged. Larger batteries would be employed for assisted motion of other body members.

A regulated power supply (or possibly a well filtered supply) 140 supplies potentiometer 60 and reference circuits (thresholds, etc.). This reduces noise in differentiating circuitry 62 and maintains accurate thresholds as the battery voltage varies during discharge.

If motor speed is not electronically controlled, a compensation circuit can be used to modify the comparator input signals as a function of battery voltage. Motor speed selection may be provided along with comparator input zone adjustment (either linked or separately). A low level battery indicator (audible and/or visual) may be employed using well known techniques.

Figure 3:
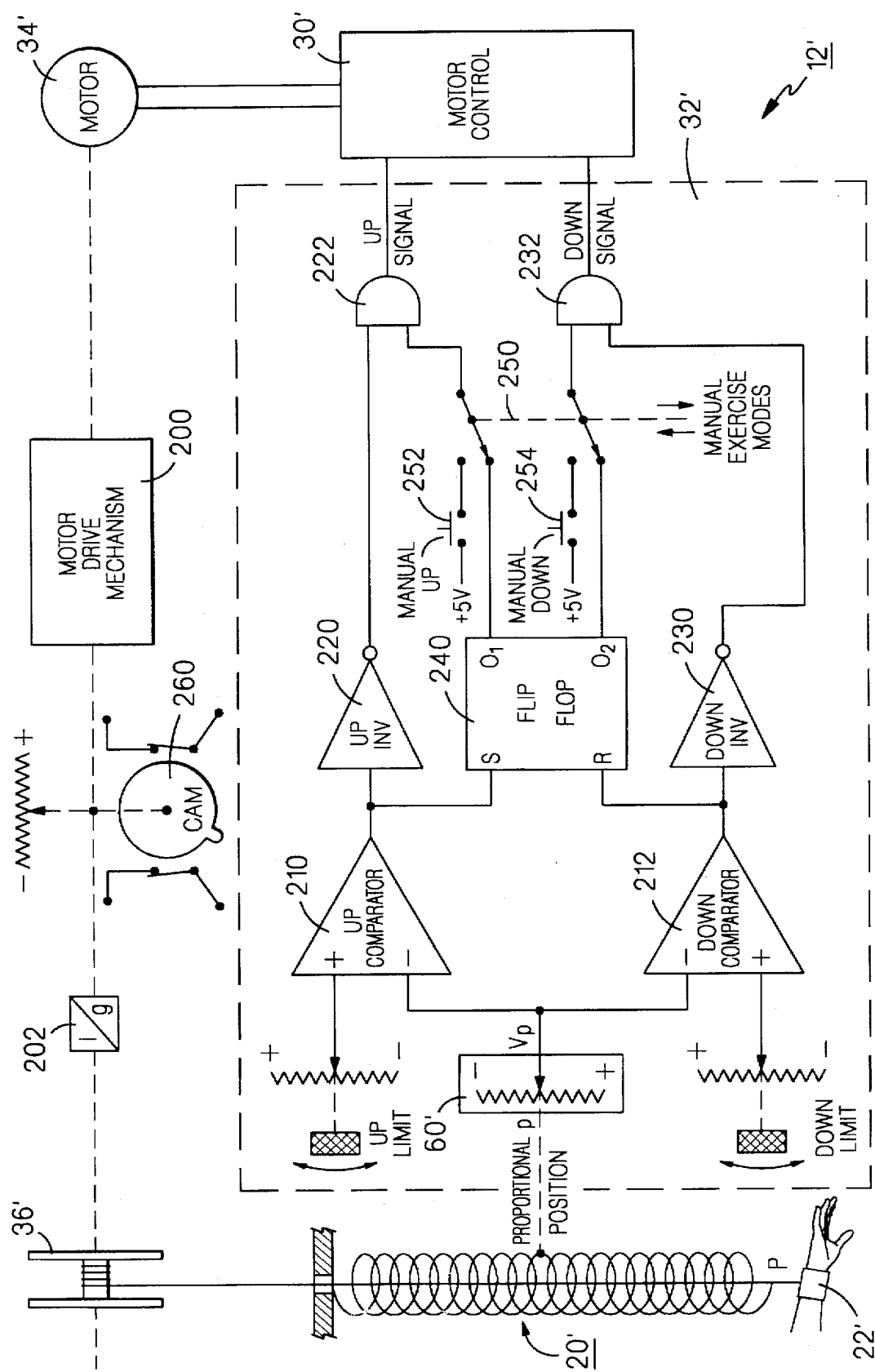
FIG. 3 is a block/schematic diagram illustrating the components and operation of a device constructed according to the invention, wherein power assist is provided in proportion to position of the arm.

FIG. 3 illustrates a simpler embodiment of the present invention, generally indicated by the reference numeral 12', in which power assist is provided as a function of position, not rate. Here a motor control 30' drives a motor 34' in response to inputs from detection and control circuitry 32'. Motor 34' is connected to rotate a pulley 36' through a motor drive mechanism 200 (similar to the drive elements illustrated on FIG. 2) and gearing 202. Pulley 36' is connected to a cuff 22' with a cable assembly 20' which may be of construction similar to that of cable assembly 20 (FIG. 2).

Detection and control circuitry 32' includes a potentiometer 60' which detects position p proportional to position P, as described above with reference to FIG. 2, and provides position input $V_p$ to UP and DOWN comparators 210 and 212, respectively. Microswitch (adjustable) limit stops (not shown) may be incorporated either alternatively or in addition to the up and down controls of circuitry 32'. Other sensors than microswitches or potentiometer 60' may be employed. Limits of UP and DOWN comparators 210 and 212 may be manually set, as indicated on FIG. 3, or perhaps adaptively modified.

The output of UP comparator 210 is connected to motor control 30' through an UP inverter 220 and an UP AND gate 222. The output of DOWN comparator 212 is connected to motor control 30' through a DOWN inverter 230 and a DOWN AND gate 232. The outputs of UP and DOWN comparators 210 and 212 are also S and R inputs, respectively, to a flip flop 240. In operation of the exercise mode, when position P reaches an extreme, the state of flip flop 240 is altered. For example, at the UP limit, output 01 of flip flop 240 goes negative and the UP inverted output also goes negative. Thus, the UP signal to motor control 30' is negative and up motion cannot occur. The output of DOWN comparator 212 is negative, the inverted signal is positive and output 02 of flip flop 240 is positive, causing DOWN AND gate 232 to be positive and motor control 30' driving motor 34' in the "down" direction. At the lower limit, the above is reversed and motor control 30' drives motor 34' in the "up" direction and the seeking of "up" and "down" limits causes device 12' to continually exercise the arm of person 10 (FIG. 1). Positive signals at inputs are required for AND gates 94 and 96 (FIG. 2B) and 222 and 232 (FIG. 3), since gate outputs remain negative if an input is open.

In the manual mode of device 12', compound switch 250 is moved to connect momentary contact switches 252 and 254, the depression of one of the latter causing "up" or "down" movement. Movement continues until a switch 252 or 254 is released or a limit is reached. When a limit is reached, the alternate switch 252 or 254 must be depressed to achieve motion away from the limit. Thus, movement may be manually controlled as desired within the limits of the settings of potentiometer 60'. Momentary contact switches 252 and 254 may be either or both mounted with the other circuitry or be paralleled with other switches wired remotely and mounted, for example, on the belt of a user or other convenient location.

A conventional cam mechanism 260 may be provided in conjunction with motor drive mechanism 200 to provide limiting signals to motor control 30'. A similar cam mechanism may also be provided in device 12 (FIG. 2), if desired.

A microprocessor (not shown) can also be used to perform the control functions, including adaptive limits and speed control.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A power assist device for a partially or totally disabled body member, comprising:
   (a) means to detect position of said body member; and
   (b) means, responsive to said means to detect, to provide powered assistance to move said body member in response to detection of said position of said body member and in proportion to rate of change of said position of said body member.

2. A device, as defined in claim 1, wherein: said means to provide powered assistance provides said powered assistance in response to rate of change of said position of said body member reaching a predetermined limit.

3. A device, as defined in claim 1, wherein: said means to provide powered assistance provides said powered assistance in response to said position of said body member reaching a predetermined position.

4. A device, as defined in claim 1, wherein said means to provide powered assistance includes:
   (a) powered assistance control means having means for attachment to a selected location on a user; and
   (b) support means for connection between said powered assistance control means and a selected location on said body member, said support means being selectively shortened or lengthened by said powered assistance control means to move said body member.

5. A device, as defined in claim 4, wherein: said means to detect detects position of a portion of said support means.

6. A device, as defined in claim 4, wherein said support means comprises:
   (a) a primary spring for connection between said powered assistance control means and said selected location on said body member;
   (b) a shorter, secondary spring connected between said selected location on said body member and a proximal end of a flexible wire; and
   (c) said wire having its distal end connected to said powered assistance control means.

7. A device, as defined in claim 6 wherein: said secondary spring is disposed coaxially internally of said primary spring and said wire has its major axis disposed coaxially internally of said primary spring and has its proximal end attached to the distal end of said secondary spring.

8. A device, as defined in claim 6, wherein: said means to detect detects linear motion of said primary spring at a location remote from said selected location on said body member.

9. A method of providing power assist for a partially or totally disabled body member, comprising:
   (a) detecting position of said body member; and
   (b) providing powered assistance to move said body member in response to detection of said position of said body member and in proportion to detected rate of change of said position of said body member.

10. A method, as defined in claim 9, further comprising: providing said powered assistance in response to rate of change of said position of said body member reaching a predetermined limit.

11. A method, as defined in claim 9, further comprising: providing said powered assistance in response to said position of said body member reaching a predetermined position.

12. A method, as defined in claim 9, further comprising:
    (a) attaching powered assistance control means to a selected location on a user;
    (b) providing support means connected between said powered assistance control means and a selected location on said body member; and
    (c) selectively shortening or lengthening said support means to move said body member in response to said detection of said position of said body member.

13. A method, as defined in claim 12, further comprising:
    (a) providing a primary spring connected between said powered assistance control means and said selected location on said body member;
    (b) providing a shorter, secondary spring connected between said selected location on said body member and a proximal end of a flexible wire; and
    (c) providing said wire having its distal end connected to said powered assistance control means.

14. A method, as defined in claim 13, further comprising: providing said secondary spring disposed coaxially internally of said primary spring and providing said wire having its major axis disposed coaxially internally of said primary spring and having its proximal end attached to the distal end of said secondary spring.

15. A power assist device for a partially or totally disabled body member, comprising:
    (a) means to detect position of said body member; and
    (b) means, responsive to said means to detect, to provide powered assistance to move said body member in response to detection of said position of said body member, said means providing said powered assistance in response to rate of change of said position of said body member reaching a predetermined limit.

16. A power assist device for a partially or totally disabled body member, comprising:
    (a) means to detect position of said body member; and
    (b) means, responsive to said means to detect, to provide powered assistance to move said body member in response to detection of said position of said body member;
    wherein said means to provide power assistance includes:
    (c) powered assistance control means attachable to a selected location on a user; and
    (d) support means connected between said powered assistance control means and a selected location on said body member, said support means being selectively shortened or lengthened by said powered assistance control means to move said body member; and
    (e) said means to detect detects position of said body member by detecting position of a portion of said support means.

17. A power assist device for a partially or totally disabled body member, comprising:
    (a) means to detect position of said body member; and
    (b) means, responsive to said means to detect, to provide powered assistance to move said body member in response to detection of said position of said body member;
    wherein said means to provide power assistance includes:
    (c) powered assistance control means attachable to a selected location on a user; and
    (d) support means connected between said powered assistance control means and a selected location on said body member, said support means being selectively shortened or lengthened by said powered assistance control means to move said body member;

and wherein said support means includes:

(e) a primary spring connected between said powered assistance control means and said selected location on said body member;

(f) a shorter, secondary spring connected between said selected location on said body member and a proximal end of a flexible wire; and (g) said wire having its distal end connected to said powered assistance control means.

18. A device, as defined in claim 17, wherein: said secondary spring is disposed coaxially internally of said primary spring and said wire is disposed coaxially internally of said primary spring and has its proximal end attached to the distal end of said secondary spring.

19. A device, as defined in claim 17, wherein: said means to detect detects linear motion of said primary spring at a location remote from said selected location on said body member.

20. A method of providing power assist for a partially or totally disabled body member, comprising:

(a) detecting rate of change of position of said body member reaching a predetermined limit; and (b) providing powered assistance to move said body member in response to detection of said rate of change of said position of said body member.

21. A method of providing power assist for a partially or totally disabled body member, comprising:

(a) detecting position of said body member; and (b) providing powered assistance to move said body member in response to detection of said position of said body member;

where providing powered assistance includes:

(c) attaching powered assistance control means to a selected location on a user;

(d) providing support means connected between said powered assistance control means and a selected location on said body member; and (e) selectively shortening or lengthening said support means to move said body member in response to said detection of said position of said body member;

and wherein providing said support means includes:

(f) providing a primary spring connected between said powered assistance control means and said selected location on said body member;

(g) providing a shorter, secondary spring connected between said selected location on said body member and a proximal end of a flexible wire; and (h) providing said wire having its distal end connected to said powered assistance control means.

22. A method, as defined in claim 21, further comprising: providing said secondary spring disposed coaxially internally of said primary spring and providing said wire disposed coaxially internally of said primary spring and having its proximal end attached to the distal end of said secondary spring.

* * * * *